United States Patent [19]

Tamai et al.

[11] Patent Number: 4,950,818
[45] Date of Patent: Aug. 21, 1990

[54] METHOD FOR TREATING ULCER

[75] Inventors: Yoshin Tamai, Shibata; Masahiro Torihara; Yoichi Kido, both of Niigata; Johji Yamahara, Ootsu; Masayoshi Ito, Yao, all of Japan

[73] Assignee: Kuraray Company, Ltd., Kurashiki, Japan

[21] Appl. No.: 369,007

[22] Filed: Jun. 21, 1989

[30] Foreign Application Priority Data

Jul. 11, 1988 [JP] Japan .................. 63-172964

[51] Int. Cl.$^5$ ..................... A61K 31/34; C07D 307/28
[52] U.S. Cl. ..................... 514/471; 514/473; 549/313
[58] Field of Search .......... 514/473; 549/313; 514/471

[56] References Cited

U.S. PATENT DOCUMENTS 4,797,417  1/1989  Okamoto et al. ............ 514/473

FOREIGN PATENT DOCUMENTS 1065877  4/1986  Japan .

OTHER PUBLICATIONS

Ito et al., "Synthesis and Spectral Characteriztion of γ Hydroxy-Δαβ-Butenolides Possessing a Conjugated Substituent in the β-Position", CA 107:237037h.

Primary Examiner—Glennon H. Hollrah
Assistant Examiner—A. A. Owens
Attorney, Agent, or Firm—Oblon, Spivak, McClelland, Maier & Neustadt

[57] ABSTRACT

A novel and useful method for treating and/or preventing ulcer in human beings is provided which comprises administering an effective amount of a pharmaceutical composition comprising at least one of the conjugated γ-oxybutenolide compounds represented by the general formula:

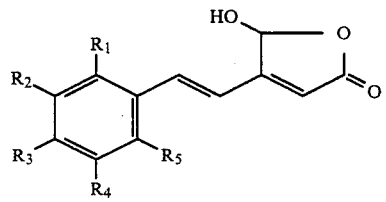

wherein $R_1$, $R_2$, $R_3$, $R_4$ and $R_5$ are the same or different and represent hydrogen atoms, alkyl groups, hydroxyl groups, alkoxy groups, nitro groups, cyano groups or halogen atoms; and optionally at least one pharmaceutically acceptable carrier.

10 Claims, No Drawings

METHOD FOR TREATING ULCER

BACKGROUND OF THE INVENTION

1. Field of the Invention

The present invention relates to a method for treating ulcer in human beings.

2. Description of the Prior Art

It has been known that the following conjugated γ-oxybutenolide compounds have a cell-killing activity on mouse neuroblastoma N18TG-2 (Int. J. Cancer, 33, 677 (1984));

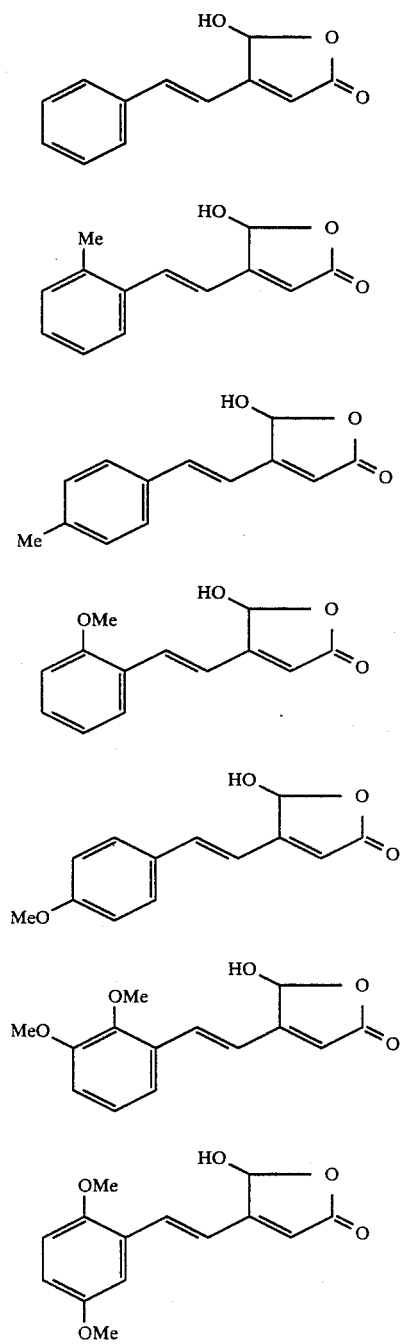

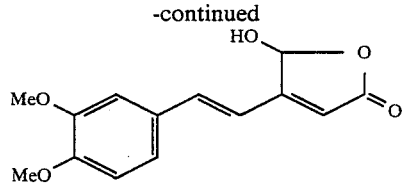

However, there has never so far been known the usefulness of these compounds as a therapeutic agent for peptic ulcer.

SUMMARY OF THE INVENTION

It is an object of the present invention to provide a novel and useful method for treating ulcers in human beings.

The above object has been accomplished by a method for treating and/or preventing ulcer in human beings which comprises administering an effective amount of a pharmaceutical composition comprising at least one of the conjugated γ-oxybutenolide compounds represented by the general formula (I):

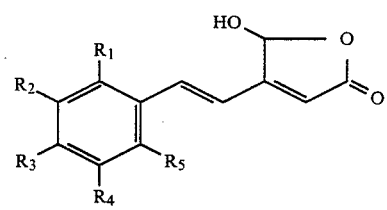

(I)

wherein $R_1$, $R_2$, $R_3$, $R_4$ and $R_5$ are the same or different and represent hydrogen atoms, alkyl groups, hydroxyl groups, alkoxy groups, nitro groups, cyano groups or halogen atoms; and optionally at least one pharmaceutically acceptable carrier.

Other objects of the present invention will be apparent according to the following disclosure.

DESCRIPTION OF THE PREFERRED EMBODIMENT

In the above general formula (I) the alkyl group preferably includes a straight or branched chain alkyl group having 1 to 6 carbon atoms such as a methyl, ethyl isopropyl, n-propyl, n-butyl, n-pentyl, isoamyl or n-hexyl group; the alkoxy group preferably includes a straight or branched chain alkoxy group having 1 to 4 carbon atoms such as a methoxy, ethoxy, propoxy or n-butoxy group; and the halogen atom includes fluorine, chlorine, bromine and iodine atoms.

Among the conjugated γ-oxybutenolide compounds represented by the general formula (I), compounds represented by the following general formula are novel compounds:

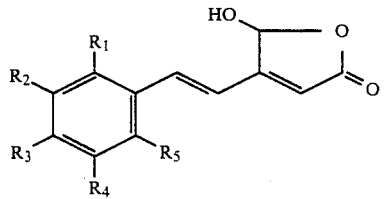

wherein $R_1$, $R_2$, $R_3$, $R_4$ and $R_5$ are the same or different and represent hydrogen atoms, alkyl groups, hydroxyl groups, alkoxy groups, nitro groups, cyano groups or halogen atoms, provided that at least one of $R_1$ to $R_5$ is not a hydrogen atom; when either of $R_1$ and $R_3$ is a methyl group or a methoxy group, at least one of the other group, $R_2$, $R_4$ and $R_5$ is not a hydrogen atom; and when $R_1$ and $R_2$, $R_2$ and $R_3$, or $R_1$ and $R_4$ are both methoxy groups, at least one of $R_3$, $R_4$ and $R_5$, $R_1$, $R_4$ and $R_5$, or $R_2$, $R_3$ and $R_5$ is not a hydrogen atom, respectively.

Examples of the conjugated γ-oxybutenolide compounds represented by the general formula (I) are enumerated below, and each compound number therein is consistently used hereinafter as indicating just the compound:

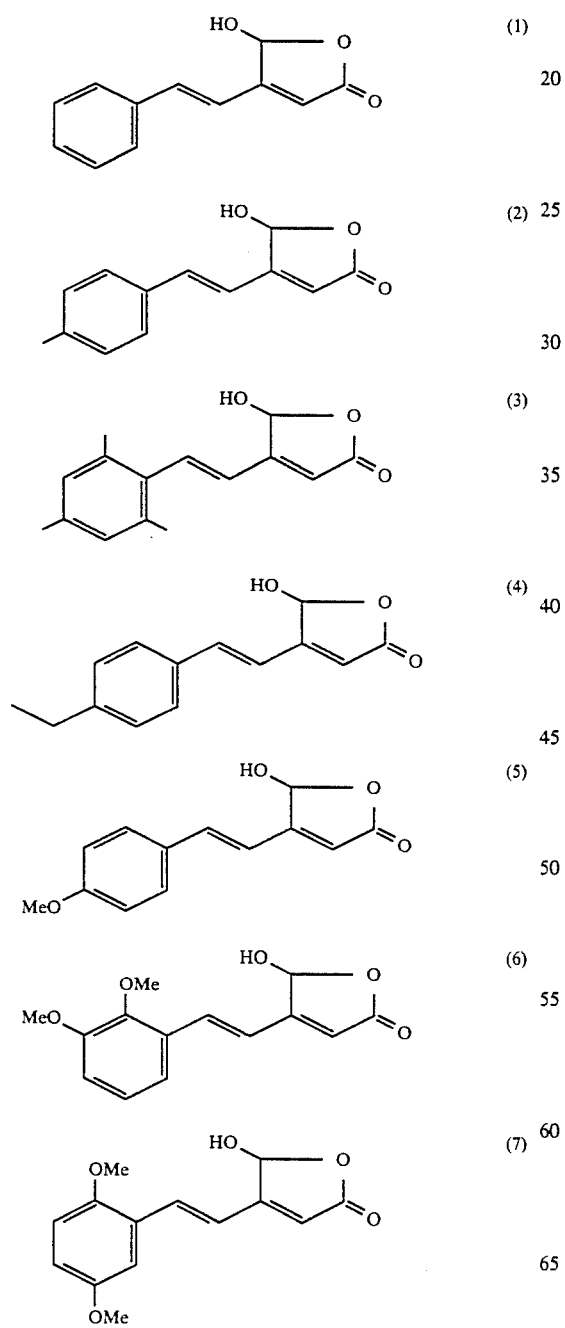

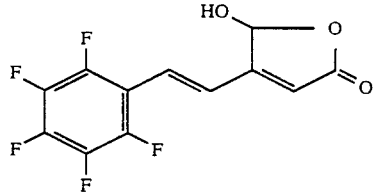

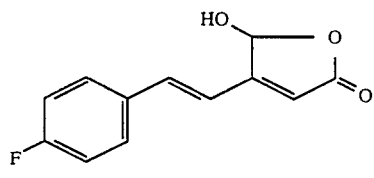

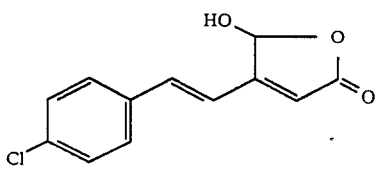

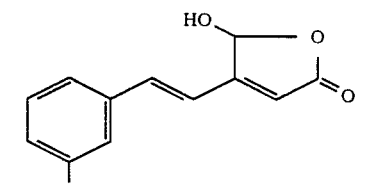

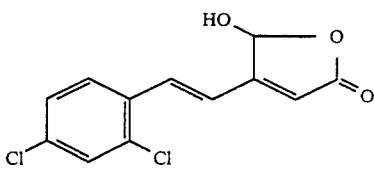

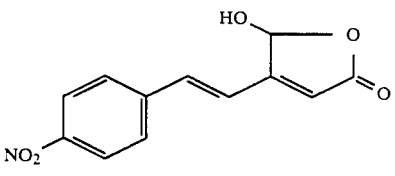

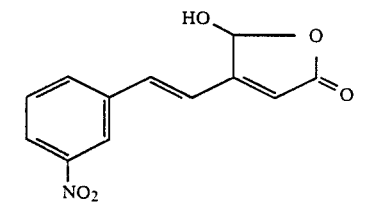

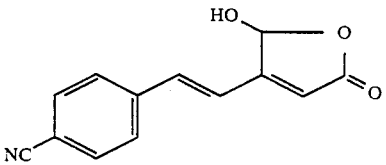

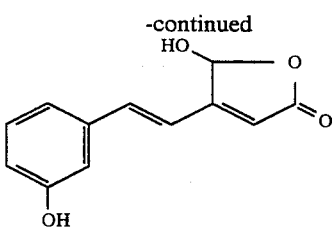

Conjugated γ-oxybutenolide compounds represented by the general formula (I) can be prepared in a manner analogous to the preparation method of known 5-hydroxy-4-[2-phenyl-(E)-ethenyl]-2(5H)-furanone (Chem. Pharm. Bull. 34 (10), 4346 (1986)).

This reaction is indicated by the following steps:

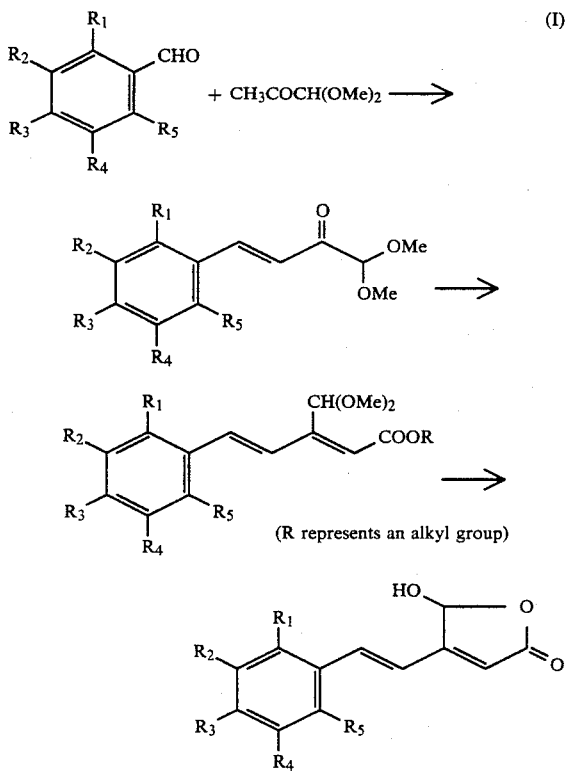

(R represents an alkyl group)

That is, a substituted or unsubstituted benzaldehyde is reacted with pyruvic aldehyde dimethyl acetal in methanol as a solvent in the presence of a base, for example an alkali such as sodium hydroxide, potassium hydroxide or barium hydroxide, or an organic base such as DBU (1,8-diazabicyclo(5,4,0)undecene-7), pyridine, piperidine or triethylamine at 0° to 65° C. (reflux temperature of methanol) for 1 to 10 hours to synthesize an (E)-1,1-dimethoxy-4-substituted or unsubstituted phenyl-3-buten-2-one. Purification can be carried out by adding water after the completion of the reaction, extracting with n-hexane, washing the separated n-hexane layer with water and distilling away n-hexane therefrom. The resulting compound is reacted with a phosphonic acid ester according to Emmons-Horner reaction to obtain a 3-dimethoxymethyl-5-substituted or unsubstituted phenyl-2,4-pentadienylcarboxylic acid alkyl ester. This reaction is carried out using conventional conditions for Emmons-Horner reaction, for example using n-BuLi, NaH, NaOMe, NaOEt or the like as a base and benzene, toluene, tetrahydrofuran or the like as a solvent inert to the reaction at around room temperature for 1 to 24 hours. Purification can be carried out by pouring the solution after the reaction into water, extracting with ether, washing the organic layer with water and distilling away ether.

The thus obtained unsaturated ester is then treated with an aqueous 20 to 50% sulfuric acid solution at room temperature to 50° C. for 1 to 10 hours to obtain a desired conjugated γ-oxybutenolide compound. In this reaction, iodine may be added to the reaction solution in an amount of 0.01 to 1.0 weight % as a reaction accelerator. Purification can readily be carried out by column chromatography or recrystallization.

Antiulcer pharmaceutical compositions for use in the treating or preventing method of the present invention may be the form of tablets, capsules, powders, granules, electuaries, or liquid preparations such as sterile solutions or suspensions for oral or parenteral administration. Tablets, granules and powders are suitable for orally administering active ingredients of the present invention, and granules and powders can, if necessary, be formulated into capsules as a unit does form. Solid agents for oral administration may contain conventional excipients such as silicic anhydride, synthetic aluminum silicate, lactose, sucrose, corn starch or fine crystalline cellulose; binders such as gum arabic, gelatin or polyvinylpyrrolidone; lubricants such as magnesium stearate, talc or silica; disintegrants such as potato starch or carboxymethylcellulose calcium; wetting agents such as polyethylene glycol, sorbitan monooleate or sodium lauryl sulfate. Tablets may be coated according to a conventional method. Liquid preparations for oral administration may be aqueous or oily suspensions, solutions, syrups, etc., or may be dry preparations which can dissolve again in a suitable vehicle prior to the use. Such liquid preparations may contain conventional emulsifiers such as lecithin or sorbitan monooleate; emulsification aids such as sorbitol syrup, methylcellulose or gelatin; non-aqueous vehicles such as coconut oil or peanut oil; antioxidants; coloring agents; flavoring agents; etc. For use in parenteral administration, a conjugated γ-oxybutenolide compound of the general formula (I) may be dissolved or suspended in a sterile vehicle to obtain a liquid preparation. The preparation of the solution may be carried out by dissolving an active compound in a vehicle for injection, filtering the solution for sterility, and pouring the solution into ampoules and sealing them. In the preparation it is preferable to add adjuvants such as local anesthetics, antiseptics or buffering agents in the vehicle. The suspension can be prepared in substantially the same manner as in the preparation of the solution except that an active compound is not dissolved but suspended in a vehicle and a procedure for sterility other than filtration is used.

Pharmaceutical compositions comprising as an active ingredient a conjugated γ-oxybutenolide compound of the general formula (I) of the present invention are effective for treatment and/or prevention of ulcers of digestive organs, particularly stomach of human beings. Although the effective amount or dose of the compounds varies depending on the extent of ulcers, the constitution of patients, kind of compounds of the general formula (I) to be used, etc., proper doses generally range from about 100 to about 2500 mg per day and per adult.

Examples of the present invention and a reference example are indicated below.

EXAMPLE 1

Antiulcer activity (HCl-ethanol ulcer)

1.5 ml of aqueous 60% ethanol solution containing 150 mM hydrochloric acid was orally administered to rats. One hour thereafter the rats were sacrificed and the length (mm) of HCl-ethanol-induced ulcer which was generated at the mucosa of the stomach was measured. Sum of the length of ulcer per animal is defined as ulcer coefficient. Specimens were each orally administered one hour before the HCl-ethanol administration. Inhibition rate was calculated by dividing the difference of ulcer coefficients of the control group and the specimen-administered group by the ulcer coefficient of the control group. The results were as shown in Tables 1-1 and 1-2.

TABLE 1

|  | Compound | Dose (mg/kg) | Animal No. | Inhibition rate (%) |
| --- | --- | --- | --- | --- |
| Test No. | Control | — | 7 | — |
| 1 | (1) | 5 | 6 | 97.9 |
| 2 | (2) | 5 | 6 | 98.3 |
| 3 | (3) | 5 | 5 | 100 |
| 4 | (4) | 2.5 | 6 | 86.2 |
| 5 | (5) | 2.5 | 6 | 98.8 |
| 6 | (6) | 1 | 6 | 59.8 |
| 7 | (7) | 5 | 6 | 98.6 |
| 8 | (8) | 1 | 6 | 67.4 |
| 9 | (9) | 5 | 5 | 100 |
| 10 | (10) | 5 | 5 | 100 |
| 11 | (11) | 2.5 | 6 | 91.0 |
| 12 | (12) | 5 | 5 | 54.1 |
| 13 | (13) | 2.5 | 5 | 34.1 |
| 14 | (15) | 5 | 5 | 99.4 |
| 15 | (16) | 2.5 | 6 | 42.7 |
| Comparative Example No. | | | | |
| 1 | Spizofurone | 100 | 5 | 86.6 |
| 2 | Teprenone | 25 | 5 | 48.9 |

Spizofurone

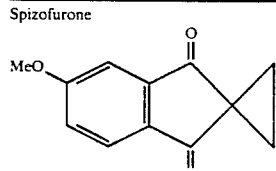

Teprenone

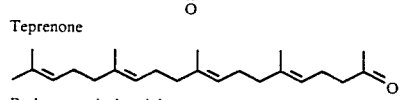

Both are typical antiulcer agents.

EXAMPLE 2

Antiulcer activity (pylorus ligation ulcer)

After rats weighing 210 to 230 g were made to fast for 24 hours, each pylorus part was ligated under ether anesthesia according to Shay et al. method [Castroenterogy, 5, 43 (1945)]. After leaving for 13 hours the animals were sacrificed, and each ulcer which had been generated at the proventriculus part was macroscopicly observed and evaluated according to the following 5 steps of ulcer index:
1; Normal
2; There are hyperemia or 5 or less of small ulcers (diameter less than 3 mm).
3; There are 5 or more of small ulcers or one large ulcer (diameter equal to or more than 3 mm).
4; There are 2 or more of large ulcers.
5; There is perforation.

Compound (1) (specimen) as prepared according to the method in Reference example and spizofurone as a control specimen were orally administered 30 minutes before the pylorus ligation. Inhibition rate was calculated by dividing the difference of ulcer coefficients of the control group and the specimen-administered group by the ulcer coefficient of the control group.

|  | Dose (mg/kg) | Animal No. | Inhibition rate (%) |
| --- | --- | --- | --- |
| Control | — | 8 | — |
| Compound (1) | 100 | 7 | 80.3 |
| Comparative example (spizofurone) | 100 | 17 | 1.5 |

EXAMPLE 3

Acute toxicity

Acute toxicity tests through oral administration were carried out using male ICR-strain mice (5 weeks old).

The $LD_{50}$ value of 5-hydroxy-4-[2-phenyl-(E)-ethenyl]-2(5H)-furanone of the present invention was 2000 mg/kg or more, and thus high safety in comparison with effective amount was ascertained.

REFERENCE EXAMPLE 1

Synthesis of 5-hydroxy-4-[2-phenyl-(E)-ethenyl]-2(5H)-furanone (Compound (1))

3 g (75 mmole) of sodium hydroxide was dissolved in 1200 g of methanol, and 159 g (1.5 mole) of benzaldehyde and 354 g (3 mole) of pyruvic aldehyde dimethyl acetal were added to the solution, and the mixture was stirred at room temperature for 7 hours.

After the completion of the reaction, 600 g of water was added thereto, and the mixture was extracted three times with each 2 l of n-hexane. The n-hexane layer was concentrated in an evaporator to obtain 269 g of the residue. GLC analysis revealed that 236.3 g of E-1,1-dimethoxy-4-phenyl-3-buten-2-one was contained in the residue.

30 g (0.75 mole) of sodium hydride was added to 300 g of toluene, followed by ice-cooling to maintain the inner temperature at 5° to 15° C., and to this mixture a solution prepared by diluting 179 g (0.8 mole) of triethyl phosphonoacetate with 150 g of toluene was dropwise added over a period of one hour. After the completion of dropwise addition, the mixture was warmed to room temperature and stirred for an additional hour. A solution prepared by diluting 120 g (0.58 mole) of the previously prepared E-1,1-dimethoxy-4-phenyl-3-buten-2-one was then added dropwise thereto over a period of 2 hours. After the completion of dropwise addition, the mixture was stirred for an additional hour and left to stand overnight.

500 ml of 10% ammonium chloride solution was added to the reaction mixture, and the mixture was twice extracted with each 1 l of isopropyl ether. The isopropyl ether layer was washed twice with each 500 ml of 10% aqueous sodium chloride and the isopropyl ether was removed by evaporation using an evaporation to obtain 203 g of the residue. GLC alanysis of the residue revealed that 72.8% of 3-dimethoxymethyl-5-phenyl-2,4-pentadiethylcarboxylic acid ethyl ester was contained in the residue.

50 ( g of this residue was dissolved in 950 ml of dioxane, 0.05 g of iodine and 700 ml of aqueous 30% sulfuric acid solution were added to the solution, and the mixture was refluxed with heating under stirring for 4 hours. After the completion of the reaction, the mixture was extracted twice with each 2 l of isopropyl ether. The isopropyl ether layer was washed with 2 l of aqueous saturated sodium chloride and isopropyl ether was removed by evaporation using an evaporator. The resulting residue was dissolved in 105 ml of benzene and 14 ml of acetone at room temperature, 35 ml of n-hexane was added thereto, and the mixture was left to stand overnight to deposit colorless crystals. The mixture was filtered, followed by drying under reduced pressure to obtain 35 g of crystals.

It was confirmed by $^1$H-NMR that these crystals were 5-hydroxy-4-[2-phenyl-(E)-ethenyl]-2(5H)-furanone.

$^1$H-NMR (270 MHz, DMSO-d$_6$/TMS): 6.20 (1H,s,10-H), 6.36(1H,s,10'-H), 7.12(1H,d,J=16 Hz,8-H), 7.28(1H,d,J=16 Hz,7-H), 7.35–7.65(5H,m,ArH), 7.80(1H,s,OH).

IR (KBr): 3220(OH), 1730($\alpha,\beta$-unsaturated $\gamma$-lactone), 1630, 1595(C=C).

m.p.: 159°–160° C.

EXAMPLES 4 to 13

Various conjugated $\gamma$-oxybutenolide compounds synthesized in the same manner as in Reference example 1 and their $^1$H-NMR spectra and infrared absorption spectra are shown in Table 2.

TABLE 2

| Compound | $^1$H-NMR (270 MHz, DMSO-d$_6$/TMS) | IR (KBr) |
|---|---|---|
| (11) | 6.22(1H,s,10-H), 6.35(1H,d,J = 8 Hz,10'-H) 7.23(1H,s,8-H), 7.23–7.60(4H,m,ArH) 7.69(1H,s,7-H), 7.82(1H,d,J = 8 Hz,OH) | 3300 (OH) 1720 ($\alpha,\beta$-unsaturated $\gamma$-lactone) 1630, 1600 (C=C) 1140 (Ar—Cl) |
| (16) | 6.19(1H,s,10-H), 6.34(1H,d,J = 6 Hz,10'-H) 6.78–7.24(4H,m,ArH), 7.01(1H,d,J = 16 Hz,8-H) 7.18(1H,d,J = 16 Hz,7-H), 7.76(1H,d,J = 6 Hz,OH) 9.41(1H,s,m-OH) | 3400 (OH) 1720 ($\alpha,\beta$-unsaturated $\gamma$-lactone) 1630, 1580 (C = C) |
| (14) | 6.29(1H,s,10-H), 6.38(1H,s,10'-H) 7.36–7.90(4H,m,ArH), 8.05(1H,d,J = 8 Hz,8-H) 8.19(1H,d,J = 8 Hz,7-H), 8.42(1H,s,OH) | 3400 (OH) 1720 ($\alpha,\beta$-unsaturated $\gamma$-lactone) 1630, 1595 (C = C) 1520 (aromatic NO$_2$) |
| (4) | 1.19(3H,t,J = 8 Hz,CH$_3$), 2.64(2H,q,J = 8 Hz,—CH$_2$—) 6.16(1H,s,10-H), 6.34(1H,d,J = 6 Hz,10'-H) 7.06(1H,d,J = 14 Hz,8-H), 7.25(1H,d,J = 14 Hz,7-H) 7.24–7.53(4H,dd(A$_2$B$_2$), ArH), 7.76(1H,d,J = 8 Hz,OH) | 3250 (OH) 1715 ($\alpha,\beta$-unsaturated $\gamma$-lactone) 1630, 1600 (C=C) |
| (13) | 6.33(1H,s,10-H), 6.40(1H,s,10'-H) 7.36(2H,s,7-H,8-H), 7.86(1H,s,OH) 7.86–8.26(4H,dd(A$_2$B$_2$),ArH) | 3300 (OH) 1720 ($\alpha,\beta$-unsaturated $\gamma$-lactone) 1630, 1600 (=C) 1510 (aromatic NO$_2$) |
| (3) | 2.23(3H,s,p-Me), 2.96(6H,s,O-Me) 6.17(1H,s,10-H), 6.40(1H,s,10'-H) 6.59(1H,d,J = 16 Hz,8-H), 6.90(2H,s,ArH) 7.34(1H,d,J = 16 Hz,7-H), 7.80(1H,s,OH) | 3350 (OH) 1730 ($\alpha,\beta$-unsaturated $\gamma$-lactone) 1630, 1615 (C=C) |
| (9) | 6.18(1H,s,10-H), 6.34(1H,brd,10'-H) 7.07(1H,d,J = 16 Hz,8-H), 7.27(1H,d,J = 16 Hz,7-H) 7.20–7.27(2H,m,ArH), 7.65–7.70(2H,m,ArH) 7.78(1H,brd,OH) | 3300 (OH) 1720 ($\alpha,\beta$-unsaturated $\gamma$-lactone) 1635, 1600 (C=C) 1230 (Ar—F) |
| (10) | 6.21(1H,s,10-H), 6.36(1H,s,10'-H) 7.14(1H,d,J = 16 Hz,8-H), 7.26(1H,d,J = 16 Hz,7-H) 7.45–7.65(4H,dd(A$_2$B$_2$),ArH), 7.80(1H,s,OH) | 3350 (OH) 1720 ($\alpha,\beta$-unsaturated $\gamma$-lactone) 1620, 1580 (C=C) 1130 (Ar—Cl) |
| (12) | 6.34(1H,s,10-H), 6.39(1H,s,10'-H) 7.22(1H,d,J = 14 Hz,8-H), 7.48(1H,d,J = 14 Hz,7-H) 7.40–7.88(4H,m,ArH,OH) | 3450 (OH) 1770 ($\alpha,\beta$-unsaturated $\gamma$-lactone) 1640, 1590 (C=C) 1120 (Ar—Cl) |
| (15) | 6.29(1H,s,10-H), 6.39(1H,s,10'-H) 7.30 (2H,s,7-H,8-H) 7.70–8.00(5H,m,ArH,OH) | 3400 (OH) 2220 (aromatic nitrile) 1720 ($\alpha,\beta$-unsaturated $\gamma$-lactone) 1630, 1600 (C=C) |

Melting points of similarly synthesized compounds (2) and (5) to (8) were as follows:
(2) 154–155° C.,
(5) 164–167° C.,
(6) 148–150° C.,
(7) 148–150° C.,
(8) 160–161° C.

EXAMPLE 14

Drug suitable for oral administration

The following components are mixed and the mixture is formulated with a tabletting machine into tablets.

| Component | Weight per tablet (mg) |
|---|---|
| Compound (3) | 100 |
| Corn starch | 50 |
| Crystalline cellulose | 100 |
| Carboxymethylcellulose | 50 |
| Total | 300 |

EXAMPLE 15

Capsule for use in oral administration

The following components are mixed in a conventional manner and this mixture is filled into hard gelatin to prepare capsules.

| Component | Weight per capsule (mg) |
| --- | --- |
| Compound (3) | 50 |
| Aluminium magnesium silicate | 150 |
| Corn starch | 100 |
| Total | 300 |

What is claimed is:

1. A method for treating and/or preventing ulcer in human beings which comprises administering an effective amount of a pharmaceutical composition comprising at least one of the conjugated γ-oxybutenolide compounds represented by the general formula:

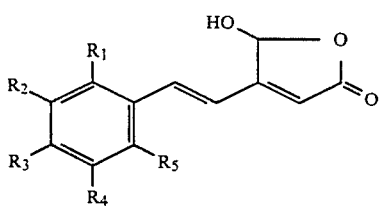

wherein $R_1$, $R_2$, $R_3$, $R_4$ and $R_5$ are the same or different and represent hydrogen atoms, alkyl groups, hydroxyl groups, alkoxy groups, nitro groups, cyano groups or halogen atoms; and optionally at least one pharmaceutically acceptable carrier.

2. A method of claim 1 wherein in the general formula the alkyl group is a straight or branched chain alkyl group having 1 to 6 carbon atoms, and the alkoxy group is a straight or branched chain alkoxy group having 1 to 4 carbon atoms.

3. A method of claim 1 wherein the ulcer is an ulcer of digestive organs.

4. A method of claim 3 wherein the ulcer is the ulcer of stomach.

5. Conjugated γ-oxybutenolide compounds represented by the general formula:

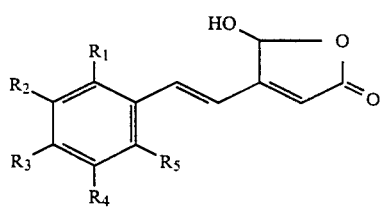

wherein $R_1$, $R_2$, $R_3$, $R_4$ and $R_5$ are the same or different and represent hydrogen atoms, alkyl groups, hydroxyl groups, alkoxy groups, nitro groups, cyano groups or halogen atoms, provided that at least one of $R_1$ to $R_5$ is not a hydrogen atom; when either of $R_1$ and $R_3$ is a methyl group or a methoxy group, at least one of the other group, $R_2$, $R_4$ and $R_5$ is not a hydrogen atom; and when $R_1$ and $R_2$, $R_2$ and $R_3$, or $R_1$ and $R_4$ are both methoxy groups, at least one of $R_3$, $R_4$ and $R_5$, $R_1$, $R_4$ and $R_5$, or $R_2$, $R_3$ and $R_5$ is not a hydrogen atom, respectively.

6. Compounds of claim 5 wherein the alkyl group is a straight or branched chain alkyl group having 1 to 6 carbon atoms, and the alkoxy group is a straight or branched chain alkoxy group having 1 to 4 carbon atoms.

7. An antiulcer pharmaceutical composition which comprises an effective amount of at least one of the conjugated γ-oxybutenolide compounds represented by the general formula:

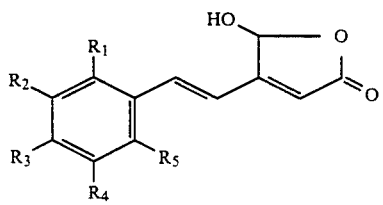

wherein $R_1$, $R_2$, $R_3$, $R_4$ and $R_5$ are the same or different and represent hydrogen atoms, alkyl groups, hydroxyl groups, alkoxy groups, nitro groups, cyano groups or halogen atoms, provided that at least one of $R_1$ to $R_5$ is not a hydrogen atom; when either of $R_1$ and $R_3$ is a methyl group or a methoxy group, at least one of the other group, $R_2$, $R_4$ and $R_5$ is not a hydrogen atom; and when $R_1$ and $R_2$, $R_2$ and $R_3$, or $R_4$ and $R_4$ are both methoxy groups, at least one of $R_3$, $R_4$ and $R_5$, $R_1$, $R_4$ and $R_5$, or $R_2$, $R_3$ and $R_5$ is not a hydrogen atom, respectively; and at least one pharmaceutically acceptable carrier.

8. A composition of claim 7 wherein in the general formula the alkyl group is a straight or branched chain alkyl group having 1 to 6 carbon atoms, and the alkoxy group is a straight or branched chain alkoxy group having 1 to 4 carbon atoms.

9. A composition of claim 7 wherein the ulcer is an ulcer of digestive organs.

10. A composition of claim 9 wherein the ulcer is the ulcer of stomach.

* * * * *